United States Patent [19]

Lindborg et al.

[11] Patent Number: 5,565,461
[45] Date of Patent: Oct. 15, 1996

[54] DERIVATIVES OF PURINE, PROCESS FOR THEIR PREPARATION AND A PHARMACEUTICAL PREPARATION

[75] Inventors: Björn G. Lindborg, Älvsjö, Sweden; Roelf Datema, Cheshire, Conn.; Karl N. G. Johansson, Enhörna; Bo F. Öberg, Uppsala, both of Sweden

[73] Assignee: Medivir AB, Huddinge, Sweden

[21] Appl. No.: 416,539

[22] Filed: Apr. 3, 1995

Related U.S. Application Data

[60] Continuation of Ser. No. 177,402, Jan. 5, 1994, abandoned, which is a division of Ser. No. 601,693, Dec. 26, 1990, Pat. No. 5,284,837.

[51] Int. Cl.⁶ ...................... A61K 31/52; C07D 473/18; C07D 473/32; C07D 473/16
[52] U.S. Cl. ................................ 514/262; 514/261
[58] Field of Search .................. 514/81, 261–3, 514/261, 262

[56] References Cited

U.S. PATENT DOCUMENTS

| | | | |
|---|---|---|---|
| 4,199,574 | 4/1980 | Schaefler | 544/276 |
| 4,565,868 | 1/1986 | Verheyden et al. | 544/276 |
| 4,590,269 | 5/1986 | Prisbe et al. | 544/276 |
| 4,714,701 | 12/1987 | Beauchamp | 544/276 |

FOREIGN PATENT DOCUMENTS

| | | |
|---|---|---|
| 56328/86 | 4/1986 | Australia. |
| 56468/86 | 4/1986 | Australia. |
| 0108285 | 5/1984 | European Pat. Off.. |
| 0141927 | 5/1985 | European Pat. Off.. |
| 0146516 | 6/1985 | European Pat. Off.. |
| 0184473 | 6/1986 | European Pat. Off.. |
| 0186640 | 7/1986 | European Pat. Off.. |
| 2134907 | 8/1984 | United Kingdom. |

OTHER PUBLICATIONS

Lundgren. J. Acquired Immune Def. Syndrome 4, 489–498 (1991).
Wyand, AIDS Res & Hum ret 8, 349(1992).
Martin et al Antiviral Res 1990, 1(Suppl) p. 114.
Wahren, Antimicrobial Agents & Chemotherapy 32(8), pp. 1137–1142 (1988).
Connolly, Antimicro. Agents & Chemo. 36, 245 (1992).
De Clercq, AIDS Res & Hum. Ret. 8, 119 (1992).
Dr. Sandstrom Letter of Jun. 19, 1990.
Mansuri et al, Chem. Tech, Sep. 1992, p. 564.
Sgari, J Med Chem 35, 3792 (1992).
Merck Standby Statement of Sep. 14, 1993.
Antiviral Agents Bulletin 6, p. 162 (Jun. 1993).
Antiviral Agents Bulletin 6, p. 260 (Sep. 1993).
Antiviral Agents Bulletin 6, 228, Aug. 1993.
Flexner, Antimicro Agents & Chemotherap 35, 2544 (1991).
Staal, AIDS Res. & Hum. Retroviruses 9, 299 (1993).
Saunders, Drug Design & Discovery, 8, 255 (1992).
Tsai. J. Infec. Diseases 169, 260 (1994).
Grand, J. Med. Primatol. 23, 256–257 (1994).
Cundy, Anti Microb Agents & Chemo. 38, 365 (1994).
Bree, J. Med. Primatol. 23, 260–261 (1994).
Tsai, J. AIDS 6, 1086 (1993).
Wakrim et al, J. Med. Primatology 23(4), pp. 247–248.
Hu et al. Med. Primatology, 23, (4), p. 239 (1994).
Bartz, J. Med. Primatology 23, 255 (1994).
Larsson et al., Antimicrobial Agents and Chemotherapy, vol. 30, No. 4, pp. 598–605 (1986).
Abele et al, Antimicrobial Agents and Chemotherapy, vol. 31, No. 1, pp. 76–80 (1987).
Bottiger, Disa, Evaluation of HIV Inhibitors in Macaques Infected with SIV and HIV-2, Dept. of Microbiology and Tumorbiology, Karolinska Institute, Stockholm, Sweden (1994).
Lake–Bakaar, Desmond et al., Antimicrobial Agents and Chemotherapy, vol. 33, No. 1, pp. 110–112 (1989).
Kuller, J. Med. Primalol. 23, 262 (1994).
Gallimore, J. Med Primatol. 23, 287 (1994).
Putkonen, J. Med. Primatol. 23, 269 (1994).
Titti, J. Med. Primatol. 23 258 (1994).
Flexner, J Infect. Diseases 170, 1394 (1994).

*Primary Examiner*—Mark L. Berch
*Attorney, Agent, or Firm*—Birch, Stewart, Kolasch & Birch, LLP

[57] ABSTRACT

The present invention is directed to a method of treating an HIV infection in a host in need of such treatment which comprises administering an effective anti-HIV amount of a compound having the formula

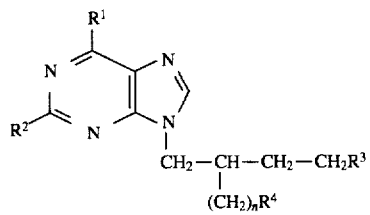

wherein:

$R^1$ is hydrogen, hydroxyl;

$R^2$ is amino;

$R^3$ and $R^4$ are independently selected from hydroxyl or an ester residue of said hydroxyl group derived from $R^6COOH$, wherein $R^6$ is hydrogen, or $C_1$–$C_3$ alkyl; and n is 1; or a pharmaceutically acceptable salt thereof.

3 Claims, No Drawings

DERIVATIVES OF PURINE, PROCESS FOR THEIR PREPARATION AND A PHARMACEUTICAL PREPARATION

This application is a continuation of application Ser. No. 08/177,402 filed on Jan. 5, 1994, now abandoned; which is a R60 Divisional Application of Ser. No. 07/601,693 filed on Dec. 26, 1990 U.S. Pat. No. 5,284,837.

FIELD OF THE INVENTION

The present invention relates to novel and known chemical compounds and pharmaceutically acceptable salts thereof for use in therapy for therapeutic and prophylactic treatment of the acquired immuno deficiency syndrome (AIDS) and infections caused by viruses requiring reverse transcriptase for replication, such as human immunodeficiency viruses and hepatitis B viruses, and also for treatment of other virus diseases, such as those of herpes viruses, diseases which include both common infections and neoplastic diseases, i.e. cancer.

BACKGROUND OF THE INVENTION

The effects of viruses on bodily functions is the end result of changes occurring at the cellular and subcelluar levels. The pathogenic changes at the cellular level are different for different combinations of viruses and host cells. While some viruses cause a general destruction (killing) of certain cells, other may transform cells into a neoplastic state.

Important common vital infections are herpes dermatitis (including herpes labialis), herpes keratitis, herpes genitalis, herpes zoster, herpes encephalitis, infectious mononucleosis and cytomegalovirus infections all of which are caused by viruses belonging to the herpes virus group. Other important vital diseases are influenza A and B which are caused by influenza A and B virus respectively. Another important common vital disease is vital hepatitis and especially hepatitis S virus infections are widely spread. Effective and selective antiviral agents are needed for treatment of these diseases as well as for other diseases caused by viruses.

Several different viruses of both DNA and RNA type have been shown to cause tumors in animals. The effect of cancerogenic chemicals can on animals result in activation of latent tumor viruses. It is possible that tumor viruses are involved in human tumors. The most likely human cases shown today are leukemias, satcomas, breast carcinomas, Burkitt lymphomas, nasopharyngeal carcinomas and cervical cancers where RNA tumor viruses and herpes viruses are indicated. This makes the search for selective inhibitors of tumorogenic viruses and their functions an important undertaking in the efforts to treat cancer.

In the late seventies a new disease was reported, which subseqently was referred to as Acquired Immuno Deficiency Syndrome (AIDS). It is now generally accepted that a retrovirus referred to as HIV (Human Immunodeficiency virus), formerly known as Human T-cell Lymphotropic Virus (HTLV-III) or Lymphadenopathy Associated Virus (LAV) plays an essential role in the etiology of AIDS. Different types of HIV have been found such as HIV-1 and HIV-2 and more are likely to be isolated.

AIDS is characterized by a profound immunodeficiency due to low numbers of a subset of lymphocyte-T-helper cells, which are one target for HIV-infection. The profound immunodeficiency in AIDS patients makes these patients highly susceptible to a variety of opportunistic infections of bacterial, fungel, protozoal or viral etiology. The etiological agents among viral opportunistic infections are often found in the herpes virus group, i.e. herpes simplex virus (HSV), Varicella Zoster virus (VZV), Epstein-Bart Virus (EBV) and, especially, cytomegalovirus (CMV). Other retroviruses affecting animals are feline leukemia virus and equine infectious anaemia virus. Human diseases such as multiple sclerosis, psoriasis and Kawasaki disease have also been reported to be associated with retrovirus infections.

Hepatitis B virus infections cause severe disease such as acute hepatitis, chronic hepatitis, fulminant hepatitis in a consider able number of persons. It is estimated that there are 200 million patients with chronic hepatitis B infection in the world. A considerable number of the chronic cases progress to liver cirrosis and liver turnouts. In some cases the hepatitis infections also take a rapid and severe course as in fulminant B hepatitis with about 90% mortality. At present there is no known effective treatment against hepatitis B infections. The replication of hepatitis B virus is similar to that of retroviruses and it contains the same essential viral reverse transcriptase activity.

GENERAL OUTLINE OF THE INVENTION

A great number of nucleoside analogues exhibit several antimetabolic activities. They do so by substituting for or competing with the naturally occuring nucleosides. Recently some nucleoside analogues have been described, which inhibit in cell culture the multiplication of human immunodeficiency virus (HIV, also called HTLV-III, LAV) the causative agent of AIDS and AIDS-related complex (ARC).

We have now found that activities for inhibition of HIV and/or herpes multiplication are exhibited by nucleoside analogues, in which the nucleoside bases are both natural and modified purine bases which in N-9 position are derivatized with an acyclic side chain, branched in the 2'-position, and containing functional groups.

PRIOR ART

Purine derivatives with antiviral activity have previously been disclosed in the following references:
9-(Phosphonylmethoxyalkyl)adenines are described in AU-A-56328/86 and AU-A-56468/86;
9-(1,3-dihydroxy-2-propoxymethyl)purines and cyclic phosphate esters are described in U.S. Pat. Nos. 4,565,868, 4,590,269 and EP-A-184 473; and
9-(4-hydroxy-3-hydroxymethylbutyl)purine derivatives are described in EP-A-141 927.
In addition the compound of the formula

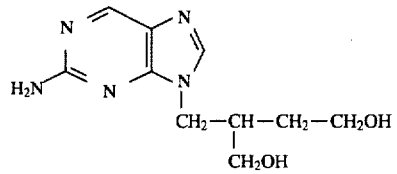

is known from EP-A-186 640; and the compounds of the formula

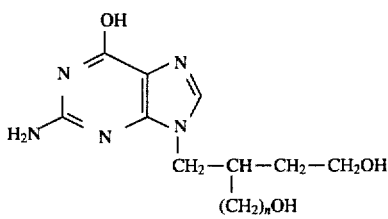

wherein n=1 or 2, are known from EP-A-146 516.

DISCLOSURE OF THE INVENTION

It has been found according to the present invention that the compounds of the formula

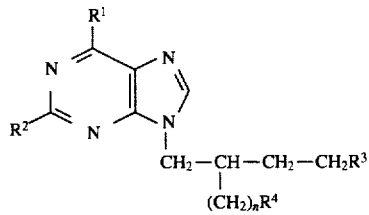

wherein:

$R^1$ is hydrogen, hydroxy, mercapto or amino;
$R^2$ is hydrogen, hydroxy, fluoro, chloro or amino;
$R^3$ and $R^4$ are independently selected from

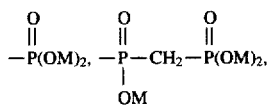

amino, hydroxy or an ether or ester residue thereof, or $R^3$ together with $R^4$ is

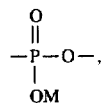

wherein

M is hydrogen or a pharmaceutically acceptable counterion; and n is 1 or 2; and pharmaceutically acceptable salts thereof, inhibit the multiplication of human immunodeficieny virus (HIV). The compounds of the formula I are useful as therapeutic and/or prophylactic agents in the control and treatment of HIV virus infections in man.

In a more general aspect, the compounds of the formula I are useful as therapeutic and/or prophylactic agents in the control and treatment of infections caused by retroviruses and hepatitis B virus in mammals and man.

All retroviruses, including HIV, require the enzyme reverse transcriptase in their natural cycle of replication.

Hepatitis B virus (HBV) is a DNA virus with a unique circular double-stranded DNA genome which is partly single-stranded. It contains a specific DNA polymerase required for vital replication. This DNA polymerase also acts as a reverse transcriptase during the replication of HBV DNA via an RNA intermediate.

The compounds of the formula I inhibit the activity of reverse transcriptase of retroviruses including HIV as well as the activity of DNA polymerase of hepatitis B virus.

Another important area of use for the compounds of the formula I is in the treatment of herpes virus infections. Among the herpes viruses may be mentioned Herpes simplex type 1 and 2, varicella (Herpes Zoster), virus causing infectious mononucleosis (i.e. Epstein-Barr virus) and cytomegalovirus. Important diseases caused by herpes viruses are herpes dermatitis (including herpes labialis), herpes genitalis, herpes keratitis, herpes encephalitis and herpes zoster.

Another possible area of use for the compounds of the present invention is in the treatment of cancer and tumors, particularly those caused by viruses. This effect may be obtained in different ways, i.e. by inhibiting the transformation of virus-infected cells to a neoplastic state, by inhibiting the spread of viruses from transformed cells to other normal cells and by arresting the growth of virus-transformed cells.

The present invention relates to the use of a compounds of the formula I

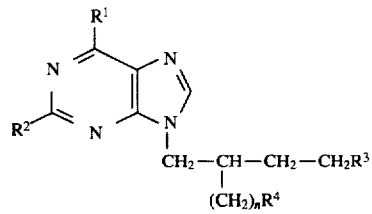

wherein:

$R^1$ is hydrogen, hydroxy, mercapto or amino;
$R^2$ is hydrogen, hydroxy, fluoro, chloro or amino;
$R^3$ and $R^4$ are independently selected from

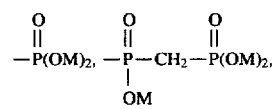

amino, hydroxy or an ether or ester residue thereof, or $R^3$ together with $R^4$ is

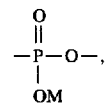

wherein

M is hydrogen or a pharmaceutically acceptable counterion; and n is 1 or 2; and pharmaceutically acceptable salts thereof for the manufacture of a medicament for therapeutic and/or prophylactic treatment of the acquired immuno difficiency syndrome and infections caused by viruses requiring reverse transcriptase for replication.

Preferably they can be used for the treatment of infections caused by HIV viruses or hepatitis B virus.

The compounds of the formula I contain one asymmetric center when $CH_2CH_2R^3$ and $(CH_2)_nR^4$ are different. Accordingly they exist in two optical forms which constitute a further aspect of the invention.

Preferred compounds to be used in accordance with the invention are those wherein $R^1$ and $R^2$ are independently hydrogen, hydroxy or amino and wherein $R^3$ is $$-\overset{O}{\underset{\|}{P}}(OM)_2,$$

hydroxy or an ester derivative thereof, and $R^4$ is OH or an ester derivative thereof or wherein $R^3$ and $R^4$ together are $$-\overset{O}{\underset{\|}{P}}\diagdown\underset{-O}{\overset{}{\diagup}}OM.$$

Preferably $R^3$ and $R^4$ are both hydroxy.

Examples of especially preferred compounds are those of the formula I

[Structure: purine ring with substituents R$^1$, R$^2$, N-CH$_2$-CH-CH$_2$-CH$_2$R$^3$ with (CH$_2$)$_n$R$^4$ branch]

wherein $R^1$=OH, $R^2$=NH$_2$, $R^3$=OH, $R^4$=OH
$R^1$=H, $R^2$=NH$_2$, $R^3$=OH, $R^4$=OH
$R^1$=NH$_2$, $R^2$=H, $R^3$=OH, $R^4$=OH
$R^1$=OH, $R^2$=NH$_2$, $$R^3 \text{ and } R^4 = -\overset{O}{\underset{\|}{P}}\diagdown\underset{-O}{\overset{}{\diagup}}OM$$

$R^1$=H, $R^2$=NH$_2$, $$R^3 \text{ and } R^4 = -\overset{O}{\underset{\|}{P}}\diagdown\underset{-O}{\overset{}{\diagup}}OM$$

$R^1$=NH$_2$, $R^2$=H, $$R^3 \text{ and } R^4 = -\overset{O}{\underset{\|}{P}}\diagdown\underset{-O}{\overset{}{\diagup}}OM$$

| | | | |
|---|---|---|---|
| $R^1$ = OH, | $R^2$ = NH$_2$, | $R^3$ = OCOC$_{1-3}$, | $R^4$ = OCOC$_{1-3}$ |
| $R^1$ = H, | $R^2$ = NH$_2$, | $R^3$ = OCOC$_{1-3}$, | $R^4$ = OCOC$_{1-3}$ |
| $R^1$ = NH$_2$, | $R^2$ = H, | $R^3$ = OCOC$_{1-3}$, | $R^4$ = OCOC$_{1-3}$ |
| $R^1$ = OH, | $R^2$ = NH$_2$, | $R^3$ = OCONH-phenyl, | $R^4$ = OCONH-phenyl |
| $R^1$ = H, | $R^2$ = NH$_2$, | $R^3$ = OCONH-phenyl, | $R^4$ = OCONH-phenyl |
| $R^1$ = NH$_2$, | $R^2$ = H, | $R^3$ = OCONH-phenyl, | $R^4$ = OCONH-phenyl |

Esters and ethers of the purine derivatives are also included in the invention. Examples of esters are phosphate esters, carboxylic esters, carbonate esters, carbamate esters or sulphonic esters. The acid part of the esters may have alkyl, aryl or arylalkyl chains, where the aryl functionalities are optionally substituted for example by alkoxy, amino, nitrile, alkyl or sulphonamido groups or by one or more halogen atoms.

Examples of other types of derivatives of the purine bases are alkyl or arylalkyl derivatives of the primary hydroxyl group(s). The arylalkyl ether derivatives may be for example benzyl or triphenyl methyl and the aryl moiety may be optionally substituted. Furthermore, it is understood that the examples of the pharmaceutically acceptable salts cited below also apply to the various esters or derivatives of the purine bases of the invention.

In a compound of the formula I $R^3$ and $R^4$ as an ether residue can be defined as OR$^5$, wherein $R^5$ is C$_{1-6}$ alkyl, arylalkyl optionally substituted with one or more alkoxy, amino, nitrile or sulphamido groups or one or more halogen atoms.

$R^3$ and $R^4$ as an ester residue can be derived from a carboxylic acid R$^6$COOH, a carbonic acid R$^7$OCOOH, a double ester of a carbonic acid R$^7$CO$_2$CH(R$^8$)OCO$_2$H, a sulphonic acid R$^7$SO$_2$OH, a carbamic acid R$^7$NHCOOH or a phosphoric acid, wherein R$^6$ is hydrogen, C$_{1-17}$ alkyl, alkoxyalkyl, arylalkyl or aryl, R$^7$ is C$_{1-17}$ alkyl, arylalkyl or aryl, R$^8$ is hydrogen or C$_{1-3}$ alkyl and said aryl and arylalkyl groups optionally can be substituted with one or more alkyl, alkoxy, amino, nitrile, sulphonamide groups or one or more halogen atoms.

Examples of pharmaceutically acceptable salts of the compounds of formula I include base salts, e.g. derived from an appropriate base, such as alkali metal (e.g. sodium, potassium, alkaline earth metal (e.g. magnesium) salts, ammonium and NX$_4$— (wherein X is C$_{1-4}$ alkyl). Physiologically acceptable acid salts include salts of organic carboxylic acids such as acetic, lactic, gluconic, citric, tartaric, maleic, malic, pantothenic, isethionic, oxalic, lactobionic and succinic acids; organic sulfonic acids such as methanesulfonic, ethanesulfonic, benzenesulfonic, p-chlorobenzenesulphonic and p-toluenesulfonic acids and inorganic acids such as hydrochloric, hydroiodic, sulfuric, phosphoric and sulfamic acids.

Physiologically acceptable counterions of the phosphonate groups include inorganic and organic counterions. Inorganic counterions are for example ammonium, sodium, potassium, lithium, magnesium and calcium. Organic counterions are derived from non-toxic bases, such as primary, secondary and tertiary amines, including naturally occuring amines. Examples of such amines are diethylamine, triethylamine, isopropylamine, ethanolamine, morpholine, 2-diethylaminoethanol, glucosamine, N-methylglucamine, piperazine and dicyclohexylamine.

The present invention also relates to novel compounds of the formula

[Structure I: purine ring with substituents R$^1$, R$^2$, and N-CH$_2$-CH-CH$_2$-CH$_2$R$^3$ with (CH$_2$)$_n$R$^4$ branch]

wherein:

$R^1$ is hydrogen, hydroxy, mercapto or amino;
$R^2$ is hydrogen, hydroxy, fluoro, chloro or amino;

$R^3$ and $R^4$ are independently selected from

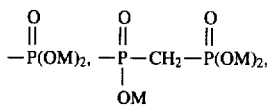

amino, hydroxy or an ether or ester residue thereof, or $R^3$ together with $R^4$ is

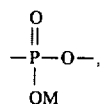

wherein

M is hydrogen or a pharmaceutically acceptable counterion;

and n is 1 or 2; with the proviso that, when $R^2$ is amino and $R^3$ and $R^4$ are hydroxy, $R^1$ is not hydroxy and in addition, when n=1, $R^1$ is not hydrogen, and pharmaceutically acceptable salts thereof.

The invention furthermore provides:

A pharmaceutical composition comprising a new compound of the formula I as active ingredient; and A method for therapeutic and/or prophylactic treatment of virus infections in an animal or human host in need of treatment comprising administering an effective amount of a new compound of the formula I.

It is a preferred aspect of the invention to treat infections caused by herpes virus or a virus requiring reverse transcriptase for replication, including human immuno deficiency viruses and hepatitis B virus.

In clinical practice the purine derivatives of the formula will normally be administered orally, by injection or by infusion in the form of a pharmaceutical preparation comprising the active ingredient in the form of the original compound or optionally in the form of a pharmaceutically acceptable carrier which may be a solid, semi-said or liquid diluent or an ingestible capsule. The compound may also be used without carrier material. As examples of pharmaceutical preparations may be mentioned tablets, dragees, capsules, granulates, suspensions, elixirs, syrups, solutions etc. Usually the active substance will comprise between 0.05 and 20% for preparations intended for injection and between 10 and 90% for preparations intended for oral administration.

In the treatment of patients suffering from retrovirus, especially HIV, or hepatitis B virus infections, it will be preferred to administer the compounds by any suitable route including the oral, parenteral, rectal, nasal, topical and vaginal route. The parenteral route includes subcutaneous, intramuscular, intravenous and sublingual administration. The topical route includes buccal and sublingual administration. The dosage at which the active ingredients are administered may vary within a wide range and will depend on various factors such as the severity of the infection, the age of patient etc., and may have to be individually adjusted. As a possible range for the amount of the compounds of the invention or a physiologically acceptable salt thereof to be administered per day may be mentioned from about 10 mg to about 10 000 mg, preferentially 100–500 mg for intravenous administration and preferentially 100–3000 mg for oral administration.

Compounds of the formula I can cooperate synergistically or additively with a wide range of other therapeutic agents, thereby enhancing the therapeutic potential of both agents without adding the toxic effects, thus increasing the therapeutic ratio.

Therefore, a compound of formula I or a pharmaceutically acceptable derivative thereof can be used in combination therapy, wherein the two active agents are present in a ratio resulting in an optimal therapeutic ratio. This can be provided either by a synergistic effect against the vital infection and/or by a decrease in toxicity while maintaining a therapeutic effect which is additive or synergistic.

The optimal therapeutic ratio is observed when the two agents are present in a ratio of 500:1 to 1:500, preferably 100:1 to 1:100, particularly 20:1 to 1:20 and especially 10:to 1:10.

Said combinations may conveniently be administered together, for example, in a unitary pharmaceutical formulation, or separately for example as a combination of tablets and injections administered at the same time or different times, in order to achieve the required therapeutic effect.

The compounds of the formula I are potentiated by interferons, other antiviral agents such as foscarnet, AZT, HIV protease inhibitors, immunomodulators, interferon inducers and growth factors.

Particularly preferred types of interferon are α, β and γ and interferon inducers such as "Ampligen" (Hem Research).

Other combinations suitable for use according to the present invention include those wherein the second agent is, for example, interleukin II, suramin, foscarnet or an ester thereof. HPA 23, inhibitors of HIV protease such as pepstatin, steroids, medications such as levamisol or thymosin to increase lymphocyte numbers and/or function as appropriate, or GM-CSF and other factors regulating cell functions.

METHODS OF PREPARATION

The compounds of the invention may be prepared by one of the following general methods, constituting a further aspect of the invention.

A. Condensing an acyclic side chain as comprised in formula I, to the N-9 position of a purine derivative. The acyclic side chain has a terminal leaving group and the functional groups may be optionally protected with known groups used for protection of hydroxy, amino or phosphonate functions.

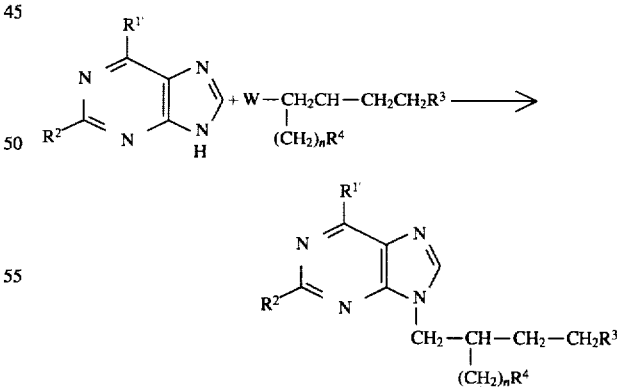

Examples of suitable derivatives of the reacting species are those wherein $R^1$ is Cl, or $R^1$ as defined above, $R^1$, $R^2$, $R^3$, $R^4$ and n are as defined above, and W is a suitable leaving groups, such as Cl, Br, J, alkyl or aryl sulfonyloxy, trifluoromethanesulfonyloxy. The condensation reaction is performed in an organic soluent such as dimethyl formamide, dimethylsulfoxyde, ethanol, acetonitrile, dichloromethane or the like at a temperature of between 0° C. and 150° C. for 1 hour to 5 days, and after condensation the products may be hydrolyzed or converted by conventional methods, known to those skilled in the art, into compounds of the formula I.

For the case of a phosphonate the side chains condensed to a purine base could be prepared in different ways. One example is the following reaction sequence, where the starting material 5-(2-bromoethyl)-2,2-dimethyl-1,3-dioxane has been described (M. R. Hamden and R. L. Jarvest, Tetrahedron Letters, Vol. 26, pages 4265–4268, 1985).

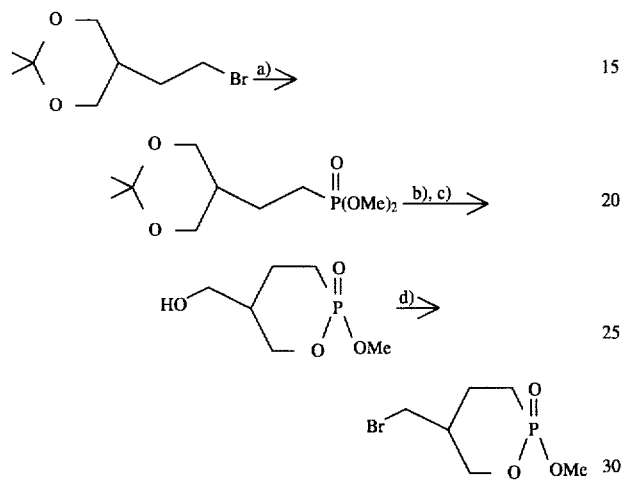

a) P(OMe)$_3$; B) H$^-$, MeOH; c) MeO$-$; d) N-bromosuccinimide, triphenylphosphine;

B. Imidazole ring closure of a substituted pyrimidine derivative to the purine base followed by removal of the protecting groups.

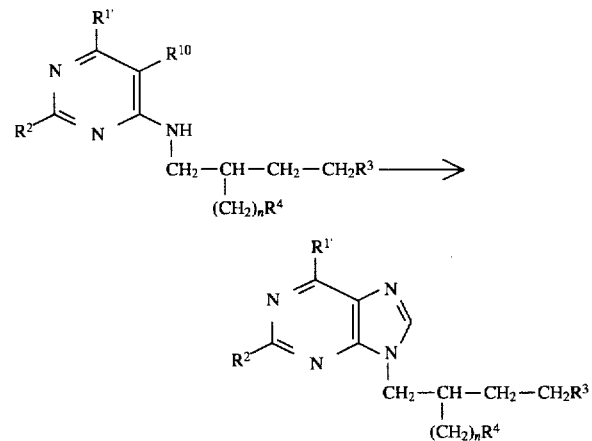

R$^1$, R$^2$, R$^3$ and R$^4$ are as defined above, R$^{10}$ is nitroso, nitro, amino or an amino derivative such as formylamino or orthoesteramino. The ring closure may be performed by known methods (the principles which are given for example by E. Lunt in Comprehensive Organic Chemistry (Eds. D. Barton and W. B. Ollis, Pergamon Press 1979) vol 4, p. 499–505 and by G. Shaw in Comprehensinve Heterocyclic Chemistry (Eds. A. R. Katritzsky and C. W. Reese, Pergamon Press 1984) vol. 5, p. 570–573. The reaction may be performed in an organic solvent such as for example, formic acid, formamide, orthoformate ester or diethoxymethylacetate at a temperature from 25° C. to 250° C. for 10 minutes to 24 hours. When R$^{10}$ is nitroso or nitro, these groups first have to be reduced to an amino group by any known method.

C. Imidazole ring closure via a furazano[3,4-d]pyrimidine ring system to the purine base followed by removal of the protecting groups.

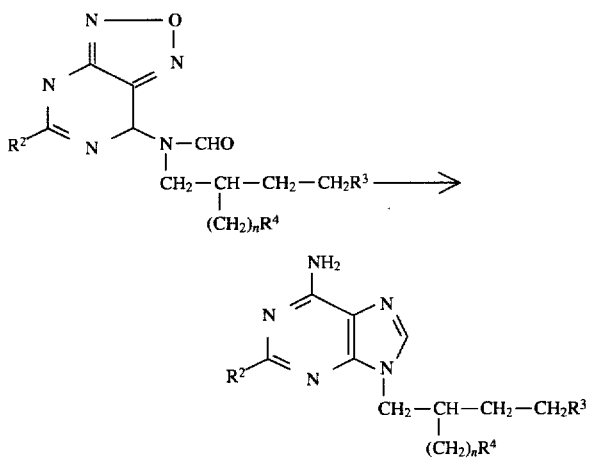

R$^2$, R$^3$ and R$^4$ are as defined above. The ring closure may be performed by heating following reductive cleavage of the furazane ring by for example zink in acetic acid. After reaction the 6-NH$_2$ group of the purine may optionally be transformed to a hydroxy group by treatment with for example sodium nitrile in acetic acid.

D. Pyrimidine ring closure to the purine base followed by removal of the protecting groups.

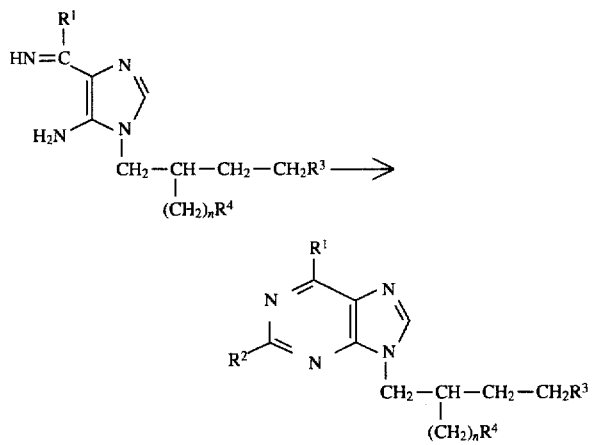

The ring closure may be performed according to known methods which have been described for example by G. Shaw in Comprehensive Heterocyclic Chemistry (Eds. A. R. Katritzsky and C. W. Reese, Pergamon Press 1984) Vol 5, p. 583–591 and by E. Lunt in Comprehensive Organic Chemistry (Eds. D. Barton and W. B. Ollis, Pergamon Press 1979) Vol. 4, p. 505–508.

The described methods A–D may be used to give mixtures of optical isomers, or in appropriate cases a single optical isomer. A compound according to the invention in the form of an optical isomer can be prepared if in method A either an optically active acyclic side chain is condensed to the N-9 position of the purine derivative or the condensation is directed to the formation of an optical isomer by means of another optically active compound, and in methods B–D starting materials having an optically active side chain are subjected to the ring closure. Additionally a single optical isomer may be obtained from the racemic mixtures by methods known per se.

The following examples will further illustrate the invention.

EXAMPLE 1

2-(2-Aminopurin-9-yl)methyl butan-1,4-diol

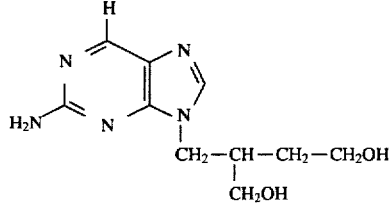

To a solution of crude dimethyl (2-aminopurin-9-ylmethyl)succinate (3.2 g, 10.9 mmol), dissolved in tert. butanol (250 ml) at 40° C., was added lithium borohydride (1.3 g, 60 mmol) in portions with stirring. After 1 hour at ambient temperature, water (30 ml) was added slowly and stirring continued over night. Inorganic salts were filtered and the solution evaporated to dryness. Yield of crude product was 1.6 g (50%). Chromatography on silica (chloroform+methanol 7+1) afforded pure product.

$^1$H NMR (DMSO-d$_6$): δ31.4 (m, 2H) C$\underline{H}_2$CH$_2$OH; 2.14 (m, 1H) CH; 3.33 (d, 2H) CH-C$\underline{H}_2$OH; 3.44 (diffuse q, 2H); 4.05 (AB part of ABX, 2H) N-CH$_2$; 6.37 (broad s, 2H) NH$_2$; 7.99 (s, 1H) H8; 8.56 (s, 1H) H6.

$^{13}$C NMR (D$_2$O): δ33.11 $\underline{C}$H$_2$CH$_2$OH; 39.58 CH; 46.34 NCH$_2$; 61.35 and 63.51 2×CH$_2$OH; 128.41 C5; 146.92 C 8; 150.48 C6; 155.05 C4; 161.50 C2.

The starting material dimethyl 2-(2-aminopurin-9-ylmethyl)succinate was prepared as follows (a,b):

a) Dimethyl 2-(2-amino-6-chloropurin-9-ylmethyl)-succinate

A mixture of 2-amino-6-chloropurine (4.07 g, 0.024 mol), dimethyl itaconate (5.00 g, 0.032 mol), and sodium hydride (55% in oil, 0.2 g) in 50 ml of dry dimethylformamide was stirred at room temperature for 3 days. About 50 ml of water was added and the mixture was washed with n-hexane (2×50 ml) and then extracted with 2×50 ml of dichloromethane. The combined CH$_2$Cl$_2$ extracts were washed with 2×20 ml of water, dried with magnesium sulfate, and evaporated in vacuum. Treatment with ether and drying afforded a white crystalline product. Chromatography (silica gel, chloroform+methanol 15+1) yielded 5.54 g (71%) or recrystallization (MeOH-H$_2$O) yielded 5.15 g (66.1%) of dimethyl 2-(2-amino-6-chloropurin-9-ylmethyl)succinate.

u/v spectrum in EtOH, λmax (nm): 310 (247).

$^1$NMR (CDCl$_3$) δ2.67 (dd, 2H) CH $_2$COO; 3.46 (m, 1H) CH; 3.70 (2 s, 2×3H) OCH$_3$; 4.42 (A$\underline{B}$X system, $\underline{J}$gem=14 Hz, 2H) NCH$_2$; 5.35 (broad s, 2H) NH$_2$; 7.79 (s, 1H) H8.

b) Dimethyl 2-(2-aminopurin-9-ylmethyl)succinate

A mixture of dimethyl 2-(2-amino-6-chloropurin-9-ylmethyl)succinate (3.28 g, 10 mmol), sodium acetate (1.5 g) and 5% palladium on charcoal (0.4 g) in ethanol (200 ml) was hydrogenated with agitation in a Parr apparatus at 40 psi for 115 h/room temperature. After filtration, sodium acetate (1.6 g) and 5% Pd/C (0.4 g) were added and the hydrogenation was continued for 70 h. After filtration and evaporation to dryness, the residue was extracted with 2×50 ml of chloroform and the combined extracts were evaporated to dryness affording 2.6 g (89%) of crude dechlorinated product.

$^1$H NMR (DMSO-d$_6$) δ8.00 (s, 1H) H8; 8.56 (s, 1H) H6.

EXAMPLE 2

2-(2-Aminopurin-9-yl)methylbutane-1,4-diol diacetate

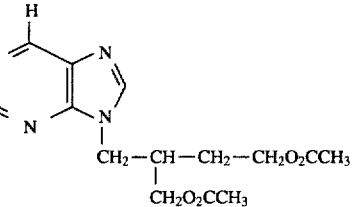

A mixture of 4-acetoxy-2-bromomethylbutyl acetate (0.465 g, 1.74 mmol), 2-aminopurine (0.282 g, 2.09 mmol), and powdered potassium carbonate (1.20 g, 8.70 mmol) in N,N-dimethylformamide (20 ml) was stirred at room temperature for 5 days. Chloroform (40 ml) was added, solid material was removed by filtration, and the solution was evaporated in vacuum to small volume. Chromatography on 50 g SiO$_2$ with chloroform+methanol (7+1) as eluent gave a fraction 70–130 ml, which was evaporated and dried in vacuum, finally at 0.1 mBar to give 0.349 g (62%) of 2-(2-aminopurin- 9-yl)methylbutane-1,4-diol diacetate. TLC on silica (chloroform+methanol 7+1): R$_f$ 0.57.

$^1$H NMR (CDCl$_3$+CD$_3$OD);δ8.64 s, 1H) H6; 7.92 (s, 1H) H8; 5.82 (broad s, 2H) NH$_2$; 4.3–4.15 (m, 4H) 2 CH$_2$OAc; 4.33 (d, 2H) CH$_2$N; 2.50 (m, 1H) CH; 2.06 (s, 6H) 2 CH$_3$COO; 1.75 (q, 2H) C$\underline{H}_2$CH$_2$OAc;$^{13}$C NMR (CDCl$_3$+ CD$_3$CD): δ170.96, 170.66 (2 C=O); 159.89 (C$_2$); 153.13 (C4); 148.77 (C6); 142.84 (C8); 126.83 (C5); 63.78 (CHCH$_2$—OAc); 61.47 (CH$_2$$\underline{C}$H$_2$OAc); 44.05 (CH$_2$N); 35.15 (CH); 27.59 ($\underline{C}$H$_2$CH$_2$O); 20.22, 20.05 (2 CH$_3$).

The starting materials were prepared by the following sequence of reactions (a–e):

a) α-Trityloxymethyl-γ-butyrolactone

A mixture of α-hydroxymethyl-γ-butyrolactone (26.83 g, 0231 mol) (G. Claeson and H.-G. Jonsson, Arkiv for Kemi 28, 167 (1967)), trityl chloride (77.3 g, 0.277 mol) and dry pyridine (200 ml) was stirred at room temperature for a few hours until homogeneous. After 10 days at room temperature the solution was poured into a mixture of 500 ml water and 500 ml n-hexane. The precipitate was washed with water and hexane and dried finally at 0.1 mBar to give 65.60 g (79%) of crude product, contaminated with some trityl alcohol. TLC on silica (ethyl acetate+n-hexane 1+3): R$_f$ 0.38.

$^{13}$C NMR (CDCl$_3$): δ177.84 (C=O); 143.71, 128.68, 127.96 and 127.20 (phenyl); 86.96 (O $\underline{C}$PH$_3$); 67.26 ($\underline{C}$H$_2$OCO); 62.49 ($\underline{C}$H$_2$OTr); 40.31 (CH); 26.15 ($\underline{C}$H$_2$CH$_2$O).

b) 2-Trityloxymethyl-1,4-butanediol

α-Trityloxymethyl-γ-butyrolactone (60.21 g, 0.168 mol) was added in small portions to a stirred suspension of lithium aluminium hydride (9.53 g, 0.251 mol) in dry tetrahydrofuran (300 ml) and the mixture was refluxed for 1 h. Slow addition of 10 ml H$_2$O+10 ml 15% NaOH and 30 ml H$_2$O produced a white sandy precipitation which was filtered off and washed with 2×50 ml tetrahydrofuran. The filtrate was evaporated to a small volume and dissolved in diethyl ether (300 ml), silica gel (250 g) was added and the mixture was carefully evaporated to a homogeneous powder. In a chromatography column the crude product—silica gel mixture was placed on top of silica gel (250 g) in n-hexane. Eluting with ethyl acetate+n-hexane (1+3), 2200 ml, removed trityl alcohol. Further eluting with ethyl acetate+ ethanol (9+1) gave fractions 2900–3700 ml (from start), which after evaporation in vacuum produced a crystallizing oil. Yield 52.77 g (87%). TLC on silica: ethyl acetate+n-hexane (1+3), R$_f$ 0.05; ethyl acetate+ethanol (9+1), R$_f$ 0.81.

c) 2-Trityloxymethyl-1,4-butanediol diacetate

To a stirred mixture of 2-trityloxymethyl-1,4-butandiol (50.85 g, 0.140 mol) and triethylamine (42.6, 0.42 mol) in dry diethyl ether (500 ml) was added slowly a solution of acetyl chloride (27.5 g 0.35 mol) in ether (25 ml) with external cooling with cold water to maintain room temperature in the mixture. After 45 min the triethylamine hydrochloride was filtered off and washed with a little ether. The combined filtrate was washed with water (50 ml), 0.5M hydrochloric acid (100 ml) and water (50 ml), dried with magnesium sulfate and evaporated in vacuum, finally at 0.1 mBar, to give 61.03 g (97%) of crude oily product. TLC on silica (ethyl aceteate+ n-hexane 1+1): R$_f$ 0.68.

d) 4-Acetoxy-2-hydroxymethylbutyl acetate

2-Trityloxymethyl-1,4-butanediol diacetate (60.90 g, 0.136 mol) was dissolved in acetic acid (320 ml) at 100° C. and water, (80 ml) was added. The solution was kept at 100° C. for 15 min, evaporated in vacuum to small volume and cooled to 0° C. The precipitate was filtered off and washed with cold ethyl acetate to give 26.44 g (theory 35.51 g) of tritylalcohol. The combined filtrate was evaporated to small volume. The compound was purified on a silica gel column (500 g SiO$_2$); eluent 0–2700 ml ethyl acetate+n-hexane (1+1), 2700–3740 ml ethyl acetate+n-hexane (2+1), then neat ethyl acetate. The fractions 2540–4800 ml were evaporated to give 14.20 g (51%) of pure 4-acetoxy-2-hydroxymethylbutyl acetate. TLC on silica (ethyl acetate+n-hexane 1+1): R$_f$ 0.30.

$^{13}$C NMR (CDCl$_3$): δ171.08, 170.88 (2 C=O); 64.07 (CH$_2$OH); 62.10, 61.45 (2 CH$_2$OAc); 37.07 (CH); 26.76 (CH$_2$CH$_2$OAc); 20.39 (2 CH$_3$).

e) 4-Acetoxy-2-bromomethylbutyl acetate

A solution of 4-acetoxy-2-hydroxymethylbutyl acetate (11.04 g, 0.054 mol) and triphenylphospine (21.27 g, 0.081 mol) in dry dichloro methane (150 ml) was stirred at 0° C., and N-bromo-succinimide (14.43 g, 0.081 mol) was added in portions. The mixture was kept at 0° C. for 20 h, evaporated to small volume and stirred with 50 ml of ethyl acetate+n-hexane (1+1). The white triphenylphospine oxide was filtered off and washed with a little ethyl acetate+n-hexane (1–1). The combined filtrate was evaporated and purified on a 200 g SiO$_2$ column with ethyl acetate+n-hexane (1+1) as eluent. The 250–550 ml fraction was evaporated in vacuum to give 11.90 g (82%) of pure 4-acetoxy-2-bromomethylbutyl acetate. TLC on silica (ethyl acetate+n-hexane 1+1): R$_f$ 0.59.

$^1$H NMR (CDCl$_3$): δ4.2–4.0 (m, 4H) 2 CH$_2$OAc; 3.53 (ABX system, 2H) CH$_2$Br; 2.25–2.1 (m, 1H) CH; 2.08, 2.06 (2 s, 2×3H) 2 COCH$_3$; 1.79 (m, 2H) CH$_2$CH$_2$OAc.

$^{13}$C NMR (CDCl$_3$): δ170.91, 170.74 (2 C=O); 64.90 (CHCH$_2$OAc); 61.71 (CH$_2$CH$_2$OAc); 36.56 (CH); 34.74 (CH$_2$Br); 28.88 (CH$_2$CH$_2$O); 20.95 (2CH$_3$).

EXAMPLE 3

9-(4-Acetoxy-2-acetoxymethylbutyl)cuanine
[2-(guanin-9-ylmethyl)-1,4-butanediol diacetate]

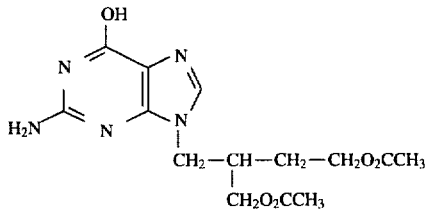
VSA 639

A mixture of 9-(4-hydroxy-2-hydroxymethylbutyl)guanine (0.50 g, 2.0 mmol), acetic anhydride (1.02 g, 10.0 mmol), pyridine (1.11 g, 14.0 mmol), and dry N,N-dimethylformamide (25 ml) was stirred at room temperature for 13 days and then evaporated to dryness in vacuum. The crystalline residue was heated with 10 ml of water and lyophilized and recrystallized from water to give 0.468 g (69%) of 9-(4-acetoxy-2-acetoxymethylbutyl)guanine.

$^{13}$C NMR (CDCl$_3$+CD$_3$OD): δ64.15 (CHCH$_2$O); 61.98 (CH$_2$CH$_2$O); 44.71 (CH$_2$N); 35.88 (CH); 27.5 (CH$_2$CH$_2$O); 20.87, 20.68 (2 CH$_3$).

EXAMPLE 4

9-(4 Propionoxy-2-propionoxymethylbutyl)guanine
[2-(guanin-9-ylmethyl)-1,4-butanediol dipropionate]

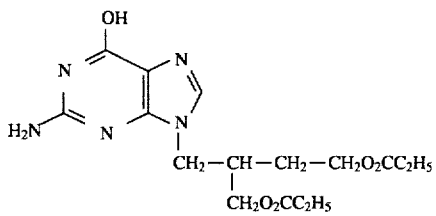
VSC 637

A mixture of 9-(4-hydroxy-2-hydroxymethylbutyl)guanine (0.50 g, 2.0 mmol), propionic anhydride (1.56 g, 12.0 mmol), pyridine (1.27 g, 16.0 mmol), and dry N,N-dimethylformamide (25 ml) was stirred at room temperature for 14 days and then evaporated to dryness in vacuum. The crystalline residue was heated with 10 ml of water and lyophilized and recrystallized from water to give 0.418 g (57%) of 9-(4-propionoxy- 2-propionoxymethylbutyl)-guanine.

$^{13}$C NMR (CDCl$_3$+CD$_3$OD): δ64.00 (CHCH$_2$O); 61.86 CH$_2$CH$_2$O); 44.78 (CH$_2$N); 35.95 (CH); 28.00 (CH$_2$CH$_2$O); 27.56, 27.44 (2 CH$_3$CH$_2$CO); 9.00 (2 CH$_3$).

EXAMPLE 5

(−)-9-(4-Hydroxy-2-hydroxymethylbutyl)guanine

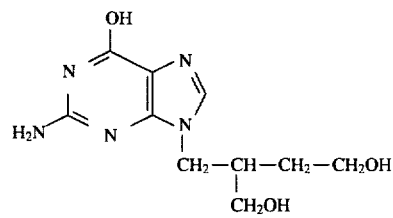
VSB 647

A solution of (−)-2-(2-amino-6-chlorpurin-9-ylmethyl)-1,4-butanediol (11.5 mg, 0.0423 mmol) in 50% aqueous formic acid (0.75 ml) was kept at 100° C./2 h and then evaporated to dryness, dissolved in 2 ml of water and lyophilized. The product was dissolved in 1 ml of water, 2 drops of conc. aqueous ammonia was added and the solution kept at 100° C. for 10 min, flushed with nitrogen to remove ammonia, and lyophilized. The residue was dissolved by warming with 1.2 ml of 20% aqueous methanol and the solution filtered and kept in open air to allow for slow partial evaporization of solvent. Crystalline needles were formed. Filtration, washing with 3 drops of water and drying yielded 6.4 mg (60%) of (−)- 9-(4-hydroxy-2-hydroxymethylbutyl)guanine.

The compound was found to be levorotatory (ethanol, 589 and 546 nm). It produced a proton NMR (DMSO-$d_6$) identical to that of the racemate. TLC on silica (ethyl acetate+methanol+water 7+2+1): $R_f$ 0.37, identical to that of the racemate.

The starting material was prepared as follows (a–b):

a) (−)-Dimethyl-2-(2-amino-6-chloropurin-9-ylmethyl)succinate

The racemic compound was resolved by repeated chromatography on a microcrystalline triacetylcellulose column, (Perstorp Biochem, Lund, Sweden) with 95% ethanol as mobile phase. The slower moving (−)-enantiomer produced a proton NMR spectrum identical to that of the racemic compound (±). The resolution was followed by proton NMR in deuterochloroform at 200 MHz with tris-[3-(heptafluoropropylhydroxymethylene)-d-camphorato]-europium(III) as chiral shift reagent. By addition of 1–1.5 parts (per weight) of shift reagent, the methyl ester signal of the racemate (2 close singlets at 3.69 and 3.695 ppm) were split into one base-line separated low-field pair (low-field signal from the (+)-enantiomer high-field signal from the (−)-enantiomer) and one less resolved high-field pair. The enantiomeric excess was then calculated from the ratio of the low-field signals.

b) (−)-2-(2-Amino-6-chloropurin-9-ylmethyl)-1,4-butanediol

To a solution of (−)-dimethyl-2-(2-amino-6-chloropurin-9-ylmethyl)succinate (enantiomeric excess 85%; 19.9 mg, 0.0607 mmol), dissolved in tert. butanol (2.0 ml) at 40° C., was added lithium borohydride (30 mg, 1.38 mmol) in portions with stirring After 1 h at ambient temperature, water (0.3 ml) was added slowly and stirring continued over night. Inorganic salts were filtered, washed carefully with tert. butanol and the solution was evaporated to dryness. Preparative thin-layer chromatography (PSC-Fertigplatten, Merck) with chloroform+methanol (5+1) as mobile phase afforded 16.5 mg (theoretical yield) of (−)-2-(2-amino-6-chloropurin-9-ylmethyl)- 1,4-butanediol. $[\alpha]_D^{20°}$ −5.20°, $[\alpha]_{546}^{20}$ −5.92° (c 0.625, ethanol). TLC on silica (chloroform+methanol 5+1): $R_f$ 0.40, identical to that of the racemate.

EXAMPLE 6

9-(4-Hydroxy-2-hydroxymethylbutyl)adenine

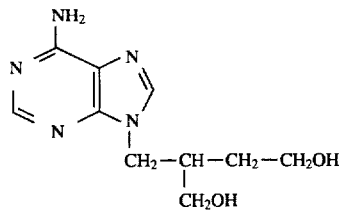

VSC 600

Dimethyl 2-(adenine-9-ylmethyl)succinate (2.93 g, 0.010 mol) was dissolved by warming with tert. butanol (120 ml), lithium borohydride (1.10 g, 0.05 mol) was added in portions and the mixture was stirred at ambient temperature for 3 h, water (10 ml) was added and stirring was continued over night. Inorganic material was filtered off and washed with tert. butanol and the filtrate evaporated to small volume. Chromatography on silica (ethyl acetate+methanol+water 7+2+1) afforded pure 9-(4-hydroxy-2-hydroxymethylbutyl)adenine.

$^{13}$C NMR (DMSO-$d_6$): δ156.24 (C6); 152.67 (C2); 150.14 (C4); 141.84 (C8); 118.88 (C5); 61.18, 58.92 (2 CH$_2$OH); 44.81 (CH$_2$N); 38.36 (CH); 32.02 ($\underline{C}$H$_2$CH$_2$OH).

The starting material was prepared as follows:
Dimethyl 2-(adenin-9-ylmethyl)succinate A mixture of adenine (5.40 g, 0.040 mol), dimethyl itaconate (8.00 g, 0.051 mol), sodium hydride (55% in oil, 0.2 g) and dry N,N-dimethylformamide (125 ml) was warmed to 120° C. and then kept with stirring at room temperature for 8 days. The precipitate was filtered, washed with dichloromethane (3×15 ml) and dried in vacuum to yield 8.96 g (76 g) of dimethyl 2-(adenin- 9-ylmethyl)-succinate.

1H NMR (CDCl$_3$);δ8.28 (s, 1H) H2; 7.90 (s, 1H) H8; 4.54 ($\underline{AB}$X system 2H) CH$_2$N; 3.70, 3.69 (2 s, 2×3H) OCH$_3$; 3.46 (m, 1H) CH; 2.72 (d, 2H) CH$_2$COO.

13C NMR (CDCl$_3$+CD$_3$OD): δ172.39, 171.42 (2 C═O); 155.61 (C6); 152.91 (C2); 149.87 (C4); 141.01 (C8); 118.85 (C5); 52.37, 51.94 (OCH3); 44.10 (CH$_2$N); 41.55 (CH); 33.30 ($\underline{C}$H$_2$COO).

EXAMPLE 7

Sodium ethyl 3-(guanin-9-ylmethyl)- 4-hydroxybutanephosphonate and 7 isomer

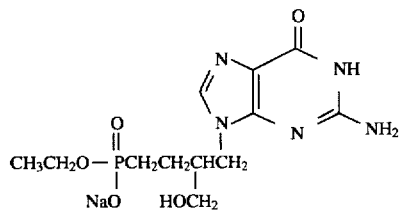

VSC 658

2-Amino-6-chloro-9-{(2-ethoxy-2-oxo-1,2-oxaphosphorinan- 5-yl)-methyl]purine (VSC 655) and its 7 isomer (100 mg, 0.29 mmol), dissolved in ethanol (4 ml), water (4 ml), and 2M aqueous sodium hydroxide (0.90 mmol) was kept at 37° C. for 18 h. The solution was neutralized by addition of weakly acidic Amberlite cation exchange resin, filtered, and evaporated to dryness to give 113 mg (quantitative yield) of a crude product.

$^1$H NMR (D$_2$O, tert BuOH, 200 MHz): δ8.01 and 7.79 (s, 8H, 7 and 9 isomers);~4.03 (m, CH$_2$N); 3.78 (quintet, CH$_2$OP); 3.50 (d, CH$_2$OH); 2.05 and 1.6–1.3 (m, PCH$_2$CH$_2$CH); 1.12 (t, CH$_3$C—O—P).

$^{13}$C NMR (D$_2$O, tert. BuOH, 50 MHz): δ161.81, 160.47, 154.12, 145.5, 142.13, 114.55, 61.74/61.42 (CH$_2$OP); 45.35 ands 45.15 (CH$_2$N); 42.25/41.91 (CH); 25.59, 22.89; 16.83 (CH$_3$C—O—P).

EXAMPLE 8

Disodium 3-(guanin-9-ylmethyl)-4-hydroxybutanephosphonate

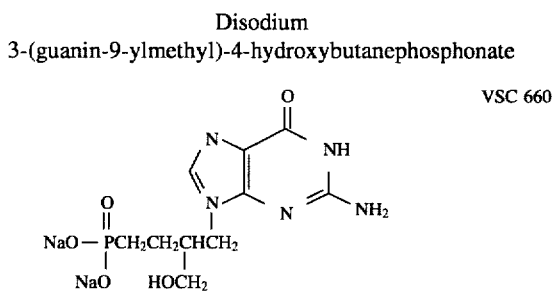

A solution of 2-amino-6-chloro-9-[( 2-ethoxy-2-oxo-1,2-oxaphosphorinan-5-yl)methyl]purine (VSC 655; 102 mg, 0.295 mmol) in ethanol (2 ml), water (2 ml), and 2M aqueous sodium hydroxide (1.0 ml, 2 mmol) was kept at 80° C. for 3 days, neutralized by addition of weakly acidic Amberlite cation exchange resin, filtered, and evaporated to dryness to give disodium 3-(guanin-9-ylmethyl)-4-hydroxybutanephosphonate.

The starting materials for examples 7 and 8 were prepared as follows:

2-(Acetoxymethyl)-4-bromobutyl acetate

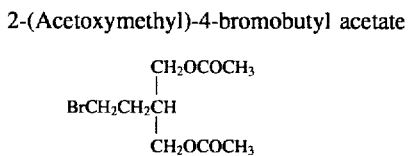

This intermediate was synthesized from 4-(acetoxy)-3-(acetoxymethyl)-butanol according to Literature Procedure. Yield 97% after flash chromatography on silica (ethyl acetate+n-hexane 1+1).

TLC $R_f$ 0.67 (SiO$_2$, ethyl acetate+n-hexane 1+1).

$^{13}$C NMR (CDCl$_3$, TMS, 50 MHz): δ170.30 (COO); 63.44 (CH$_2$O); 36.27 (CH); 31.67 (Br—CH$_2$); 30.29 (Br—C—CH$_2$); 20.51 (CH$_3$).

Diethyl 4-acetoxy-3-(acetoxymethyl)butanephosphonate

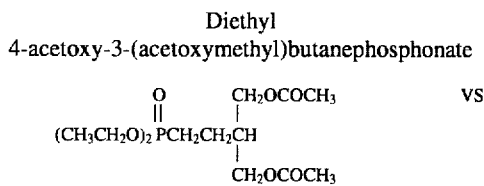

Triethyl phosphite (2.70 g, 16.3 mmol) was added with stirring to 2-(acetoxymethyl)-4-bromobutyl acetate (VSC 647, 3.95 g, 14.8 mmol) at 180°–190° C. and stirring was continued at 190° C. for 0.5 h. The residue was evaporated in vacuum and kept at ca. 0.1 mB. Flash chromatography on silica with ethyl acetate+ethanol (9+1) yielded 3.36 g (70%) of product.

TLC $R_f$ 0.57 (SiO$_2$, ethyl acetate+ethanol 9+1).

$^{13}$C NMR (CDCl$_3$, TMSD, 50 MHz): δ170.37 (COO); 63.22 (CH$_2$OAc); 61.30/61.18 (CH$_2$OP, J 6 Hz); 37.58/37.27 (CH, J 16 Hz); 24.11/21 29 (CH$_2$—C—P, J 142 Hz); 20.97/20.90 (CH$_2$P J 4 Hz); 20.46 (CH$_3$COO); 16.20/16.08, J 6 Hz.

(2-Ethoxy-2-oxo-1,2-oxaphosporinan-5-yl)methanol (racemic cis-trans mixture)

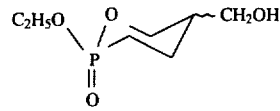

VSC 648 (1.05; 3.24 mmol) was dissolved in 16 ml of a 0.5 molar solution of sodium ethoxide in ethanol. The solution was warmed to 50° C. and then kept at 37° C. for 2 h. After evaporation to dryness in vacuum, the residue was extracted with ethyl acetate and purified by flash chromatography on silica with ethyl acetate+ethanol (9+1) as eluent. Yield 0.462 g (74%) of VSC 650 in an isomeric (cis-trans) ratio of 0.36/1.00.

TLC $R_f$ 0.2.6 (SiO$_2$; ethyl acetate+ethanol 9+1).

$^{13}$C NMR (CDCl$_3$, TMS, 50 MHz); major isomer—minor isomer): δ72.22/72.08–70.64/70.52 (CH$_2$O in ring, J 6 Hz); 62.18–63.64 (CH$_2$OH); 60.81/60.69–61.35/61.23 (CH$_2$—O—P, J 6 Hz); 38.87/38.75–37.39/37.27 (CH, J 6 Hz); 24.69/24.52–23.35/23.18 (CH$_2$—P, J 8 Hz); 23.06/20.48–21.38/18.80 (CH$_2$—C—P, J 129 Hz); 16.25/16.15 (CH$_3$—C—O—P, J 5 Hz).

5-(Bromomethyl)-2-ethoxy-2-oxo-1,2-oxaphosphorinane (racemic cis-trans mixture

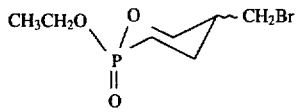

N-Bromosuccinimide (2.67 g, 15 mmol) was added in portions to a stirred, ice-chilled solution of 2-ethoxy-2-oxo-1,2-oxaphosphorinan-5-yl)methanol (VSC 650, 1,944 g, 10 mmol) and triphenyplhosphine (3.97 g, 15 mmol) in 40 ml of dichloromethane, and stirring was continued for 16 h at 4° C. After evaporation in vacuum, diethyl ether (50 ml) was added and the mixture shaken and stirred vigorously. The crystallized triphenylphosphine oxide was removed by filtration and washed with several portions of ether. The combined extracts were evaporated to dryness and purified by flash chromatography on silica with ethyl acetate+ethanol (9+1). Yield 1.569 g (61%) of VSC 654 in a cis-trans ratio of 0.7/1.0. TLC Rf 0.57 (SiO$_2$ ethyl acetate+ethanol 9+1).

$^{13}$C NMR (CDCl$_3$, TMS, 50 MHZ, major isomer—minor isomer): δ71.76/71.61 (CH$_2$O in ring, J 6 Hz); 60.74/60.62–61.20/61.08 (CH$_2$—O—P, J 16 Hz); 37.56/37.44–37.10/36.98 (CH, J 6 Hz); 32.13–31.67 (CH$_2$Br); 26.66/26.49–25.37/25.23 (CH$_2$P, J 7 Hz) 22.60/20.02–20.90/18.32 (CH$_2$—C—P, J 129.4 Hz); 16.13/16.01 (CH$_3$—C—O—P, J 6.1 Hz).

2-Amino-6-chloro-9-[(2-ethoxy-2-oxo-1,2-oxaphosphorinan-5-yl)methyl]purine and 7 isomer

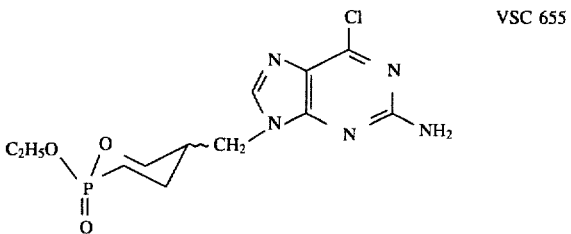

A mixture of 5-(bromomethyl)-2-etoxy-2-oxo-1,2-oxaphosphorinane (VSC 654; 0.353 g, 1.82 mmol), 2-amino-6-chloropurine (0.50, 2.95 mmol), anhydrous potassium carbonate (0.50 g, 3.62 mmol), and DMF (15 ml) was stirred at room temperature for seven days. Chloroform (30 ml) was added, and after filtration, the solution was evaporated to small volume in vacuum. The residue was purified by flash chromatography on silica (chloroform+methanol 5+1). Yield 0.282 g (45%) as a cis-trans and 7–9 isomeric mixture.

TLC$_{Rf}$ 0.74 and 0.68 for 7 and 9 isomer, respectively (SiO$_2$, chloroform+methanol 5+1).

1H NMR (CDCl$_3$, TMS, 200 MHz): δ7.80 and 7.76 (s, H8, 7 and 9 isomer); 5.4 (broad s, NH$_2$); 4.3–4.1 (m, CH$_2$OP); 4.02 (d, CH$_2$N); 2.5–2.4 and 2.1–1.7 (m, CHCH$_2$CH$_2$P); 1.37 (dt, CH$_3$—COP).

$^{13}$C NMR (CDCl$_3$, TMS, 50 MHz): δ159.38 (C$_2$); 153.93 (C4); 143.50 (C8); 70.91/70.79–69.94/69.79 (CH$_2$O in ring, J 7 Hz) 61.79 to 61.45 (2 d, CH$_2$—O—P, J 7 Hz); 44.35 and 43.25 (CH$_2$N); 36.68/36.56–35.05/34.93 (CH, J, 6 Hz); 25.88/25.74–24.18/24.04 (CH$_2$P, J 7 Hz); 22.99/20.41–21.16/18.59 (CH$_2$—C—P, J 129 Hz); 16.59/16.47 (CH$_3$—C—O—P, J 6 Hz).

Biological tests

Test I Effect of compounds of the formula I on HIV in H9 cells

Materials and methods: HIV infection of H9 cells

H9 cells, 105 cells per well on a 24 well plate, suspended in 2 ml RPMI-medium containing 10% fetal calf serum, 100 μg/ml pencillin, 10 μg/ml streptomycin sulfate and 2 μg/ml polybrene are exposed to HIV (HTLV-IIIB) and different concentrations of the test compounds. The plates are incubated at 37° C. in 5% CO$_2$ for 6–7 days. The contents in each well is then homogenized with a pipette and transferred to a centrifuge tube. After centrifugation for 10 min at 1500 rpm the supernatant is removed and the cell pellet is analyzed by fixing in methanol on glass plates. Human HIV positive serum diluted 1:80 or 1:160 is added and incubated for 30 min at 37° C., The plate is then washed with phosphate-buffered saline (PBS) containing Ca2+ and Mg2+. Sheep antihuman conjugate (FITC) is added and after a new incubation the plate is again washed with PBS. Contrast staining is done with Evans blue and after drying the frequency of HIV antigen containing cells is determined in a microscope. The test result is shown in Table I.

TABLE I

| Compounds | IC$_{50}$M |
| --- | --- |
| Concentration (μM) for 50% inhibition (IC$_{50}$) of human immuno deficiency virus multiplication in cell culture | |
| 9-[4-hydroxy-2-(hydroxymethyl)butyl]-guanine (VSA 671) | 1–10 |
| (-)-9-[4-hydroxy-2-(hydroxymethyl)butyl]-guanine (VSB 647) | 0.1–7 |
| (-)-9-[4-hydroxy-2(hydroxymethyl)butyl]-guanine (VSB 648) | 0.1–7 |
|  | 1–5 |
|  | 1–5 |
| 9-[4-hydroxy-2-(hydroxymethyl)butyl]-guanine (VSC 600) | 10 |

Table I shows that the tested compounds are active inhibitors of HIV virus multiplication.

Test II Cellular toxicity

H9 cells, 2×107 cells per plate, are incubated in RPMI-1640 medium containing 10% fetal calf serum, 70 mg/l penicillin, 100 mg/l streptomycin and 10 mM hepes, in absence or presence of test-compounds. The number of cells per plate is determined after 48 h. Cells incubated in the absence of test compounds then underwent two cell division cycles.

F5000 cells, which are human embryo cells, 1×105 cells per plate, are incubated in Eagle's minimal essential medium, supplemented with Earle's salts, non-essential amino acids, 10% fetal calf serum, 10 mM hepes, 70 mg/l penicillin and 100 mg/l streptomycin, in absence or presence of test compounds. The number of cells per plate is determined after 48 h. Cells incubated in the absence of test compounds underwent one cell division cycle. The results are given as % inhibition of cell multiplication when the concentration of the compounds is 100 μM or 250 μM.

TABLE II

Cellular toxicity on H9 and F5000 cells

| Compound | % inhibition (concentration μM) | |
| --- | --- | --- |
|  | H9 | F5000 |
| 9-[4-hydroxy-2-(hydroxymethyl)-butyl]guanine (VSA 671) | 55 (500) | 55(1000) |
| (-)-9-[4-hydroxy-2-(hydroxymethyl)-butyl]guanine (VSB 647) | 5 (100) |  |
| 9-[4-hydroxy-2-(hydroxymethyl)butyl]-adenine (VSB 600) | 25 (200) | 25 (500) |
| 2-(2-aminopurin-9-yl)methyl-butan-1,4-diol (VSB 212) |  | 20 (500) |
|  |  | 75 (500) |

Table II shows that the concentrations at which the compounds exhibit toxicities, vastly exceed the concentrations needed for 50% inhibition of HIV multiplications as given in Table I.

Test III Oral bioavailability

Oral bioavailability was determined by dosing the animals (cynomologous monkeys and rats) intravenously and orally on separate occasions with the compounds. Blood samples were taken after appropriate intervals for determination of drug level in plasma. Appropriate pharmacokinetic calculations were then carried out based on plasma concentration against time relationship.

TABLE III

Oral bioavailability of compound determined as VSA 671

| Compound | F*% |
| --- | --- |
| Monkey | |
| 9-[4-hydroxy-2-(hydroxymethyl)butyl]guanine (VSA 671) | 10 |
| 2-(2-aminopurin-9-yl)methylbutane-1,4-diol-diacetate (VSC 610) | 32 |
| Rat | |
| 9-[4-hydroxy-2-(hydroxymethyl)butyl]guanine (VSA 671) | 11 |
| 9-[4-acetoxy-2-(acetoxymethyl)butyl]guanine.HCl (VSC 640) | 20 |
| 9-[4-propionoxy-2-(propionoxymethyl)butyl]guanine.HCl (VSC 641) | 19 |
| 2-(2-aminopurin-9-yl)methylbutan-1,4-diol (VSB 212) | 26 |

*Plasma AUC (area under curve) of compound relative to AUC after intravenously given VSA 671.

From the table can be seen how the plasma concentration of VSA 671 is significantly increased after VSA 671 has been given as a 6-deoxy prodrug (VSB 212), and ester (VSC 600 VSC 641) or an ester of 6-deoxy prodrug (VSC 610).

We claim:

1. A method of treating a HIV infection in a host in need of such treatment which comprises administering an effective anti-HIV amount of a compound having the formula

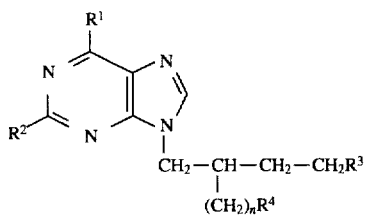

wherein:

R¹ is hydrogen, hydroxyl;

R² is amino;

R³ and R⁴ are independently selected from

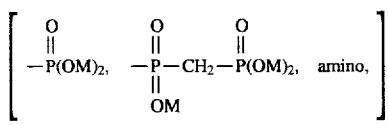

hydroxyl, or an ester residue of said hydroxyl group derived from $R^6COOH$, wherein $R^6$ is hydrogen, or $C_1$–$C_3$ alkyl and n is 1; or a pharmaceutically acceptable salt thereof.

2. The method according to claim 1 in the form of the R(−) isomer.

3. The method according to claim 1, wherein said compound is the R(−) isomer and has the formula

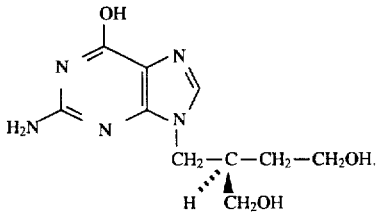

\* \* \* \* \*

UNITED STATES PATENT AND TRADEMARK OFFICE
CERTIFICATE OF CORRECTION

PATENT NO. : 5,565,461
DATED : October 15, 1996
INVENTOR(S) : Lindborg et al.

It is certified that error appears in the above-identified patent and that said Letters Patent is hereby corrected as shown below:

On the title page:
 After Section [60] with regard to Related U.S. Application Data, insert the following section:

--[30] Foreign Application Priority Data
May 6, 1988 [SE]   Sweden ............... 8801729-8 --

Signed and Sealed this

Twentieth Day of May, 1997

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,565,461
DATED : October 15, 1996
INVENTOR(S) : LINDBORG, Bjorn Gunnar et al It is certified that error appears in the above-indentified patent and that said Letters Patent is hereby corrected as shown below:

Claim 1

Line 9, counting the formulas as one line, delete the following formula:

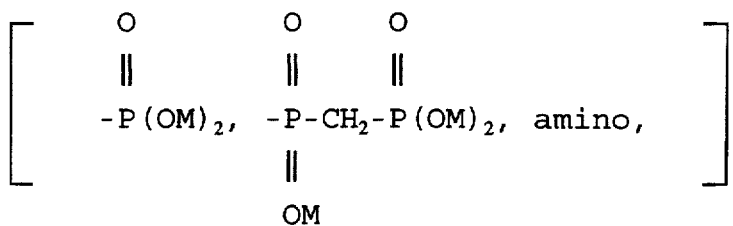

Line 11, counting the formulas as one line, after "$C_1$-$C_3$ alkyl" insert -- ; -- (semi-colon)

Signed and Sealed this

Twenty-sixth Day of August, 1997

Attest:

BRUCE LEHMAN

Attesting Officer      Commissioner of Patents and Trademarks